(12) United States Patent
Bernabei

(10) Patent No.: US 6,518,538 B2
(45) Date of Patent: Feb. 11, 2003

(54) METHOD AND APPARATUS FOR PLASMA SKIN RESURFACING

(75) Inventor: Gian Franco Bernabei, Florence (IT)

(73) Assignee: Mattioli Engineering Ltd., London (GB)

( * ) Notice: Subject to any disclaimer, the term of this patent is extended or adjusted under 35 U.S.C. 154(b) by 0 days.

(21) Appl. No.: 09/975,559

(22) Filed: Oct. 12, 2001

(65) Prior Publication Data

US 2002/0043520 A1 Apr. 18, 2002

Related U.S. Application Data

(60) Provisional application No. 60/240,980, filed on Oct. 18, 2000.

(51) Int. Cl.[7] .................................................. B23K 9/00
(52) U.S. Cl. ........................ 219/121.52; 219/121.59; 219/121.48; 607/101; 607/96; 607/2
(58) Field of Search ................ 219/121.52, 121.59, 219/121.48, 121.37, 121.38; 607/101, 104, 96, 1, 2

(56) References Cited

U.S. PATENT DOCUMENTS

| 5,643,322 A | * | 7/1997 | Ito et al. ........................ 604/20 |
| 5,800,545 A | * | 9/1998 | Yamada et al. ................ 623/15 |
| 5,836,944 A | | 11/1998 | Cosmescu ....................... 606/41 |
| 5,972,013 A | | 10/1999 | Schmidt ....................... 606/185 |
| 6,315,738 B1 | * | 11/2001 | Nishikawa et al. .......... 600/583 |

FOREIGN PATENT DOCUMENTS

| DE | 297 24 247 | 8/2000 |
| WO | WO 98/35618 | 8/1998 |

* cited by examiner

Primary Examiner—Mark Paschall
(74) Attorney, Agent, or Firm—Foley & Lardner

(57) ABSTRACT

A radio frequency generated plasma is provided to a skin surface in a controlled manner, in order to heat and selectively damage a thin superficial layer, thereby inducing a renewal process of the epidermis. The plasma is generated by providing a vacuum to the probe, and also providing an rf pulse to an electrode within the probe, thereby creating a glow discharge that includes gas ions that contact the skin and cause the skin to heat up.

6 Claims, 2 Drawing Sheets

METHOD AND APPARATUS FOR PLASMA SKIN RESURFACING

RELATED APPLICATIONS

This application claims the benefit of priority from U.S. provisional patent application 60/240,980, filed Oct. 18, 2000.

BACKGROUND OF THE INVENTION

1. Field of the Invention

The present invention relates to a method and apparatus for applying to the skin, in a controlled manner, a radio frequency generated plasma in order to heat and selectively damage thin superficial layers of the skin, thereby inducing a renewal process of the epidermis.

2. Description of the Related Art

It is well known in the skin treatment art that in order to renew the epidermis layer, induced damage of the skin is required. One such method uses laser radiation that is incident on the skin and that generates several effects on the skin, depending on the wavelength of the laser radiation, the pulse duration of the laser energy applied to the skin, and the radiation energy provided to the skin.

The most commonly used method is $CO_2$ laser radiation for generating a superficial heating of the skin. When laser light reaches the skin, its intensity decreases exponentially as it progresses down into lower layers of the skin. This means that the thermal energy that is delivered is higher in the first layer and decreases exponentially as its progresses down to lower layers of the skin. Moreover, the first corneum stratus of the skin has a higher absorption than other layers. Such an energy profile is not suitable for a uniform heating of a volume of skin due to the fact that in the superficial (upper) layers, the reached temperature is too high and in the lower layers the reached temperature is not high enough to trigger the desired skin treatment process.

SUMMARY OF THE INVENTION

The present invention utilizes a method and apparatus of heating a superficial portion of skin using a combined action of radio frequency and a plasma generated by the same radio frequency.

Two principles are used in the present invention. First, radio frequency currents are localized in the external layer of the skin due to the skin effect, and thus the heating is localized in a thin (upper) layer of skin.

It is well known that an alternating voltage applied to a conductor generates a current on the external layer of the conductor and the depth depends on the frequency and the resistance of the conductor (so-called skin effect).

Second, the plasma generated at the contact of the skin, due to the radio frequency and a high vacuum generated by a suitable pump, is composed of high energy gas ions that strike the surface of the skin, thereby generating heat in the superficial layer of the skin.

The interaction with the skin has some similarities to the interaction described in the patent application entitled "Method and Apparatus For Skin Brown Spot Removal", patent application Ser. No. 09/361,407, which is incorporated in its entirety herein by reference.

One advantage of such an approach is by not having electrodes in contact with the skin, a more even distribution of the radio frequency current in the skin is achieved. Also, there is achieved a combined action from the striking gas ions and a more accurate control of the power applied to the skin surface, due to the higher impedance of the plasma that controls the current independently from the electrical conductivity value of the skin.

The present invention relates to an apparatus and a method for skin resurfacing treatment, which provides induced thermal damage of the skin by radio frequency heating and by ion bombardment of the skin.

This dual effect may be achieved by using a pulsed radio frequency generator connected to a probe for coupling to the skin. The probe is preferably made of a non-conductive material (such as glass or plastic), and enables the application of a high vacuum to the skin surface (e.g., 5–10 millibars) over a predetermined (e.g., round) portion of the skin, by using a non-conductive pipe connected to a vacuum pump. At a suitable distance (around 10 millimeters) from the surface of the skin, an electrode (that is housed within the probe) is used to generate a radio frequency field between the electrode itself and the surface of the skin. After reaching a sufficient vacuum (e.g., 5–10 millibars of atmospheric pressure), a high voltage radio frequency electric field is applied between the electrode and the surface of the skin, due to a radio frequency pulse applied to the electrode. Such a radio frequency field triggers a glow discharge inside the probe between the electrode and the skin. A radio frequency current, due to the low impedance of the glow discharge, flows evenly on the surface of the skin, and, due to the skin effect, is limited to the glow discharge area in a depth of about 300 microns. In the surrounding tissues, the current density decreases by the square of the distance from the area covered by the glow discharge within a depth of 300 microns. Moreover, the high energy ions of the glow discharge strike the surface of the skin, thereby providing a plasma skin resurfacing that can be used to remove spider veins, skin brown spots, or port wine stains, for example.

The present invention provides a controlled heating of a selected portion of the skin to a depth of about 300 microns. As a result, it is possible to reach a desired temperature of 70 degrees C. or more, which triggers controlled damage to the skin cells to achieve. a desired effect. The temperature reached in the described volume of the skin depends primarily on the selected pulse length and the power of the radio frequency generator. Preferably, a temperature reached in the described volume of the skin is a temperature in the range of from 75 degrees C. to 95 degrees C.

To achieve a substantially uniform heating of a volume of the skin, a method according to the invention includes:

1) Application of a probe to the skin, where the probe is held against an open area on the skin of about one square centimeter, where the probe includes an electrode at a distance of 10 millimeters (plus or minus a few millimeters) from the skin surface, and where a vacuum suction pipe is connected to the probe.

2) Generation of a high vacuum inside the probe and at the surface of the skin by connection of the probe to a high vacuum pump, by way of the vacuum suction pipe.

3) Application of high voltage at a frequency of 21 MHz in the probe between the electrode and the skin, by way of a pulsed radio frequency generator connected to the probe by way of a conductive cable.

4) Generation of a glow discharge for a time less than 1 second sustained by a power less than 500 W.

BRIEF DESCRIPTION OF THE DRAWINGS

The invention will become more fully apparent from the following detailed description when read in conjunction with the accompanying drawings with like reference numerals indicating corresponding parts throughout, and wherein.

DETAILED DESCRIPTION OF THE PREFERRED EMBODIMENTS

Preferred embodiments of the present invention will be described in detail hereinbelow, with reference to the drawings.

According to the present invention, a probe is put in contact with the skin to be treated (e.g., so as to remove spider veins or brown spots or port wine stains from the skin surface, for example).

Figure 1:
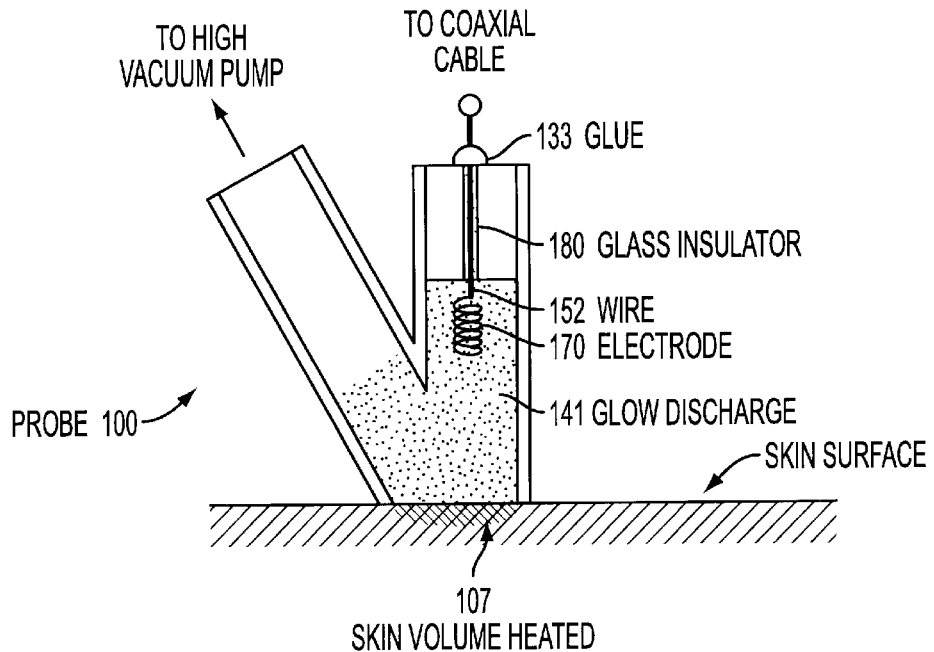
FIG. 1 shows a probe that may be utilized to treat a skin surface in order to provide relatively uniform skin heating, in accordance with a first embodiment of the invention.
Figure 2:
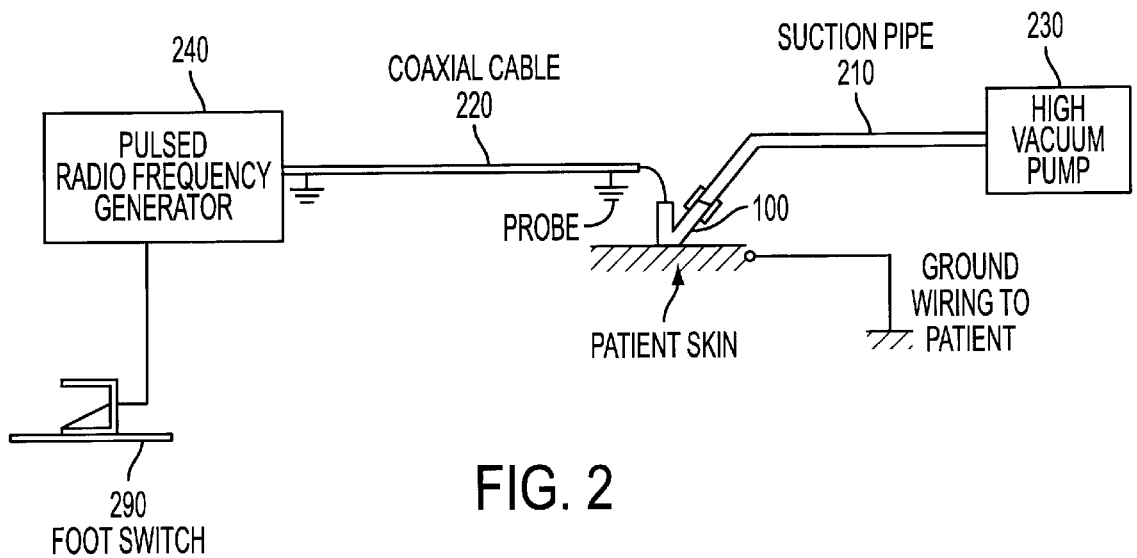
FIG. 2 shows a system that may be utilized to treat a skin surface to provide relatively uniform skin heating, in accordance with the first embodiment of the invention.

In a first embodiment of the invention, as seen in FIG. 1, the probe 100 is. V-shaped and is preferably made from polycarbonate. However, other types of plastic materials or glass or suitable insulating material may be used for the probe 100. Referring now to FIGS. 1 and 2, a first upper end of the V-shaped probe 100 is connected to a vacuum suction pipe 210, and a second upper end of the V-shaped probe 100 is connected to a coaxial cable 220. The coupling of the vacuum suction pipe 210 to the first upper end of the probe 100 and the coupling of the coaxial cable 220 to the second upper end of the probe 100 are air-tight couplings. That way, a vacuum can be formed within the probe 100. The bottom end of the V-shaped probe 100 has an opening that is to be placed in direct contact with a portion of the skin to be treated (shown as cross-hatched area 107 in FIG. 1), to provide an air-tight coupling of the opening against the skin surface.

The opening of the probe 100 preferably has a smooth round edge in order to assure a tight coupling with the skin and to avoid vacuum leakage. The opening is preferably round in shape, but any other shape can be used. In the first embodiment, the opening has a diameter of 8 millimeters, but other sizes may be utilized while remaining within the scope of the invention. For example, a larger diameter opening may be used by increasing the stroke of the vacuum pump 230, the diameter of the suction pipe and the power of the radio frequency generator 240. The power of the radio frequency generator 240 should be increased linearly with the increase of the surface covered by the glow discharge, in order to obtain substantially the sa me temperature on the skin.

The first upper end of the V-shaped probe 100 is connected to the coaxial cable 220 by way of a glass insulator 180 fed through to the probe 100. The glass insulator 180 covers one end of the coaxial cable 220 that is coupled to the probe 100. A copper wire 152 is incased within the glass insulator 480, and is preferably welded to a terminal end of an inner wire of the coaxial cable 220.

In case of feeding of gas, as in the second embodiment to be described later, the upper part of the probe is modified in order to enable a flow of gas between the copper wire and the glass insulator. Glass is used instead of plastic for the wire insulator within the probe, due to the high temperature that the electrode reaches during the operation of the probe for treating a patient's skin. Other materials, such as ceramic, could be used as well. A suitable glue 133 is used in order to assure that the vacuum is tight and that no leaks occur between the copper wire 152 and the glass insulator 180 at the top portion of the probe 100 in the view of FIG. 1).

In the first embodiment, an electrode 170 is formed at a distal end of the copper wire 152, where the copper wire is wound by several turns with a diameter of about 1 millimeter for each of the turns, thereby forming the electrode 170. For example, five turns are used in the first embodiment, but other numbers of turns, as well as turn diameters, may be used while keeping within the scope of the invention. A glow discharge emanates from the electrode 170 when subject to pulsed radio frequency energy. The electrode 170 is disposed within the probe 100 in such as manner as to not be in contact with either the walls of the probe 100 or the surface of the skin. As explained above, the copper wire 152 is fitted inside the glass insulator 180 and is connected with an inner conductor (wire) of the coaxial cable 220, so as to receive radio frequency energy from the radio frequency pulse generator 240 by way of the coaxial cable 220.

The distance between the last turn of the electrode 170 (that is furthest from the coaxial cable 220) and the bottom opening of the V-shaped probe 100 is preferably 10 millimeters. That range may be varied (e.g., 5–20 mm range, for example) to provide a desired temperature to the skin. The positioning of the turns of the electrode 170 and the copper wire 152 is such that the turns are orthogonal to the surface of the opening, in order to have an even distribution of the electric field as it impinges on the surface of the skin.

The first upper end of the V-shaped probe 100 is connected through the suction (or vacuum) pipe 210 to the high vacuum pump 230. In the first embodiment, an oil rotary pump is used which can provide up to a 5 millibar vacuum.

In the first embodiment, the coaxial cable 220 has a length of 2.3 meters, and is used as an impedance transformer from the low impedance output of the radio frequency generator 240 (52 ohm) to the probe 100, to provide for a glow discharge at a desired (e.g., 21 MHz) frequency. Other cable length are suitable at different frequencies and with other types of radio frequency generators, as well as high voltage radio frequency transformers.

The radio frequency generator 240 used in the present invention may be a conventional power generator having a pulse duration that is selectable, and having an output power capability of up to 500 W. The triggering of a pulse may be done by a footswitch 290, for example, or by other ways (e.g., toggle switch on the housing of the radio frequency generator 240). A preferred pulse duration is a value of between 1 milliseconds and 1000 milliseconds. An output power of the radio frequency generator 240 may be between 1 and 500 W, depending on the desired temperature to which the skin surface is to be heated. Also, the output radio frequency may be a value within the range of between 2 MHz and 52 MHz. Upon selecting a different frequency, the depth of the heated volume of the skin by the radio frequency current vary, i.e., the higher the frequency, the less the depth. The cable length of the coaxial cable 220 is chosen in order to match the high impedance of the glow discharge with the low impedance of the radio frequency pulse generator 240, and is approximately one-fourth of the wavelength of the radio frequency traveling inside the coaxial cable 220.

When the probe 100 is placed in contact with a desired area of a patient's skin to be treated, the vacuum pump 230 is activated. Upon reaching a vacuum pressure of 10 millibars or less, the footswitch 290 is then activated, thereby enabling the generation of the radio frequency voltage. The radio frequency voltage travels along the coaxial cable 220 to the electrode 170, whereby a glow discharge is generated due to the vacuum within the probe 100. The glow discharge within the probe 100 is shown as the gas-like region 141 in FIG. 1. As seen in FIG. 2, the patient is preferably grounded, to enhance the attraction of the gas ions within the glow discharge to the patient's skin.

Radio frequency current as well gas ions are applied to the surface of the skin under the opening of the probe 100. Gas ions of the glow discharge act as a conductor, enabling the flow of current. When the gas ions strike the surface of the skin at high speed, they penetrate inside and they lose their charge, thus enabling the flow of current.

The frequency generator 240 is switched off after the pre-selected pulse width of radio frequency energy has been applied to the probe 100. This enables the reaching of a desired superficial temperature of the skin, so as to generate a desired amount of heat damage of the skin cells under the probe 100 (so as to remove port wine stains or spider veins or skin brown spots, for example).

Figure 3:
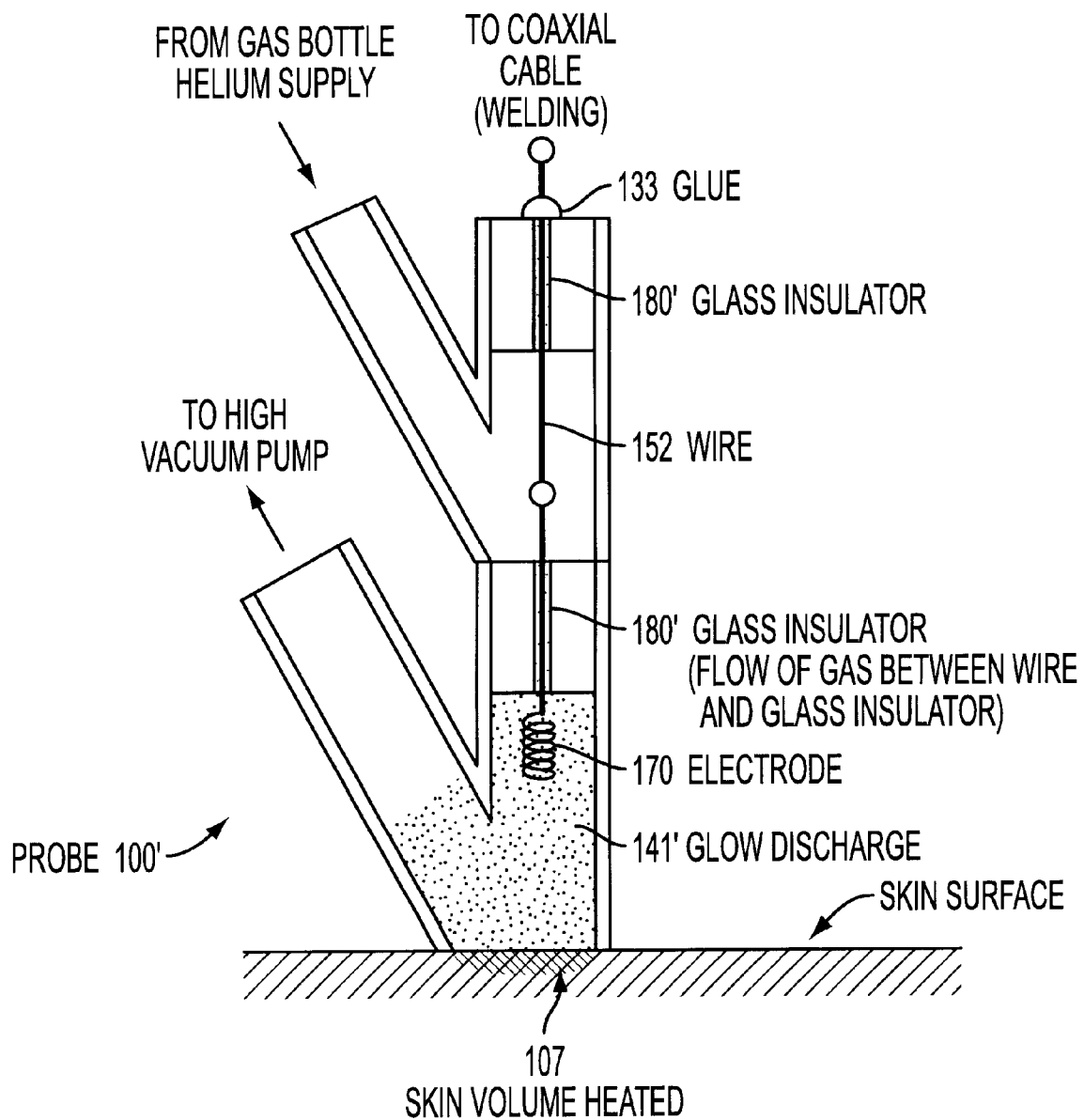
FIG. 3 shows a probe that may be utilized to treat a skin surface, in accordance with a second embodiment of the invention.

In a second embodiment of the invention, as shown in FIG. 3, a supply of low pressure gas, such as Helium, is provided to a third input port of the probe 100' in order to maintain a gas of controlled composition at a desired vacuum pressure (e.g., 10–50 millibars) over the skin. This low pressure gas is provided by a gas source (e.g., external canister of gas) that feeds the gas through an additional (third) input port of the probe 100'. As in the first embodiment, the first input port of the V-shaped probe 100' is connected to the radio frequency pulse generator 240 by way of a coaxial cable 220, and the second input port of the V-shaped probe 100' is connected to the vacuum source 230 by way of the vacuum pipe 210, to thereby provide a vacuum or near-vacuum condition within the probe 100'. In the second embodiment, the glass insulator 180' has an opening to expose a portion of the copper wire 152 to the flow of helium gas supplied from the third input port of the probe 100'. This enables a flow of gas between the copper wire 152 and the glass insulator 180', to provide a more stable glow discharge within the probe 100'.

In this second embodiment, the low pressure gas is supplied at a pressure of between 10–50 millibars, in order to stabilize the glow discharge and to selectively inject ions in the skin. Other gases besides Helium may be utilized while remaining within the scope of the invention, for example, Nitrogen or Oxygen or mixtures of gas including Helium may be used instead of Helium only.

While the present invention has been described with respect to the preferred embodiments, other types of configurations may be possible, while remaining within the spirit and scope of the present invention, as exemplified by the claims.

What is claimed is:

1. An apparatus for treating a skin surface of a patient, comprising:

a probe having an opening to be in contact with the skin surface, the probe further having a first input port and a second input port;

a radio frequency generator that provides a radio frequency voltage;

a vacuum pump that provides a vacuum;

a suction pipe connected between the vacuum pump and the probe, the suction pipe providing the vacuum to the probe via the first input port;

a coaxial cable that provides the radio frequency voltage to the probe via the second input port;

an electrode disposed within the probe and connected to the coaxial cable, the electrode configured to receive the radio frequency power generator and to provide a glow discharge when the vacuum is provided to the probe by way of the vacuum and the vacuum pump, wherein the glow discharge provides a substantially uniform heating of the skin surface down to at least a predetermined depth beneath the skin surface.

2. An apparatus according to claim 1, wherein the treating of the skin surface is to resurface the skin.

3. A method for treating a skin surface, comprising:

controlling a pulsed radio frequency generator to output at least one pulse having an output power of between 1 and 500 W, an output frequency of between 2 MHz and 52 MHz, and an output pulsewidth of between 1 and 1000 millisecond;

controlling a vacuum source to provide a vacuum;

providing the at least one pulse and the vacuum to a probe to be provided directly on the skin surface to be treated, the probe having an opening that covers the skin surface to be treated, the probe further having an electrode which receives the least one pulse and which is under vacuum due to the vacuum provided by the vacuum source, wherein a glow discharge is provided to the skin surface as a result, in order to provide a substantially uniform heating of the skin surface and regions below the skin surface to a fixed depth therebelow.

4. A method for treatment of a skin surface according to claim 3, wherein treatment is to remove unwanted brown spots from the skin surface.

5. A method for treatment of a skin surface according to claim 3, wherein low pressure Helium is injected in the glow discharge.

6. A method for treatment of a skin surface according to claim 3, wherein treatment is to resurface the skin.

* * * * *